(12) United States Patent
Weishaupt et al.

(10) Patent No.: US 9,649,097 B2
(45) Date of Patent: May 16, 2017

(54) OCCLUDER

(75) Inventors: Andreas Weishaupt, Baar (CH); Jerome Bernhard, Zurich (CH)

(73) Assignee: CARAG AG, Baar (CH)

( * ) Notice: Subject to any disclaimer, the term of this patent is extended or adjusted under 35 U.S.C. 154(b) by 586 days.

(21) Appl. No.: 14/118,233

(22) PCT Filed: May 15, 2012

(86) PCT No.: PCT/EP2012/059048
§ 371 (c)(1),
(2), (4) Date: Feb. 7, 2014

(87) PCT Pub. No.: WO2012/156415
PCT Pub. Date: Nov. 22, 2012

(65) Prior Publication Data
US 2014/0155932 A1    Jun. 5, 2014

(30) Foreign Application Priority Data

May 17, 2011 (EP) .................................. 11166363

(51) Int. Cl.
*A61B 17/08* (2006.01)
*A61B 17/00* (2006.01)
*A61B 17/12* (2006.01)

(52) U.S. Cl.
CPC .... *A61B 17/0057* (2013.01); *A61B 17/12109* (2013.01); *A61B 2017/00575* (2013.01);
(Continued)

(58) Field of Classification Search
CPC A61B 2017/00606; A61B 2017/00575; A61B 2017/00597; A61B 2017/00619;
(Continued)

(56) References Cited

U.S. PATENT DOCUMENTS 3,874,388 A   4/1975   King et al.
4,836,204 A   6/1989   Landymore et al.
(Continued)

FOREIGN PATENT DOCUMENTS

CN   2251364 Y   4/1997
CN   1224999 A   8/1999
(Continued)

OTHER PUBLICATIONS

International Search Report for PCT/EP2012/059048 mailed Aug. 17, 2012.

*Primary Examiner* — Gregory Anderson
*Assistant Examiner* — Christina Lauer
(74) *Attorney, Agent, or Firm* — McDonnell Boehnen Hulbert & Berghoff LLP (57) ABSTRACT

An Occluder for occluding a passage in a circulatory system comprises at least one occluding body (4), for occluding the passage, an expanding unit (1) comprising at least one fixation structure for fixing the occluding body (4, 5) within the passage, wherein at least a part of the expanding unit (1) is expanding into said fixation structure thereby expanding the occluding body and a locking unit (2, 3) for locking the expanding unit (1) in its expanded state. The expanding unit (1) comprises a first and a second end and wherein the first end is attached to a first element of the locking unit (2, 3) and the second end is attached to a second element of the locking unit (2, 3), the first and second elements of the locking unit (2, 3) being brought in locking engagement with each other when the occluding body (4, 5) is expanded, wherein the occluder further comprises a jacket (6, 7) which envelops at least a part of the expanding unit (1). This occluder ensures that no parts of the occluder can wander within the human or animal body and enhances the growth of the body tissue over the occluder.

12 Claims, 8 Drawing Sheets

(52) U.S. Cl.
CPC ............... *A61B 2017/00592* (2013.01); *A61B 2017/00597* (2013.01); *A61B 2017/00606* (2013.01); *A61B 2017/00619* (2013.01)

(58) Field of Classification Search
CPC .... A61B 17/12109; A61B 2017/00703; A61B 17/0057
See application file for complete search history.

(56) References Cited

U.S. PATENT DOCUMENTS

| | | | |
|---|---|---|---|
| 5,709,707 A | 1/1998 | Lock et al. | |
| 6,488,706 B1* | 12/2002 | Solymar ............ | A61B 17/0057 623/3.1 |
| 2002/0156499 A1 | 10/2002 | Konya et al. | |
| 2003/0149463 A1 | 8/2003 | Solymar et al. | |
| 2004/0220610 A1 | 11/2004 | Kreidler et al. | |
| 2005/0273135 A1 | 12/2005 | Chanduszko et al. | |
| 2008/0077180 A1 | 3/2008 | Kladakis et al. | |
| 2008/0249562 A1* | 10/2008 | Cahill ............... | A61B 17/0057 606/215 |
| 2010/0324538 A1 | 12/2010 | Van Orden | |

FOREIGN PATENT DOCUMENTS

| | | |
|---|---|---|
| EP | 0474887 | 3/1992 |
| EP | 1149561 A1 | 10/2001 |
| WO | 9716119 A1 | 5/1997 |
| WO | 9741779 A | 11/1997 |
| WO | 0149185 A1 | 7/2001 |
| WO | 0238051 A2 | 5/2002 |
| WO | 03032818 A2 | 4/2003 |
| WO | 2005034723 A2 | 4/2005 |
| WO | 2005074813 A1 | 8/2005 |
| WO | 2005110240 A1 | 11/2005 |
| WO | 2010151509 A1 | 12/2010 |
| WO | 2011/003213 A1 | 1/2011 |

* cited by examiner

OCCLUDER

CROSS REFERENCE TO RELATED APPLICATIONS

This application is a U.S. National Phase Application pursuant to 35 U.S.C. 371 of International Application No. PCT/EP2012/059048 filed on May 15, 2012, which claims priority to European patent application 11166363.9, filed May 17, 2011, the disclosures of which are incorporated herein by reference in their entirety.

TECHNICAL FIELD

The present invention relates to an occluder for occluding a passage in a circulatory system and more particularly for closing a body passage of a human body, for example an aperture through the atrial septum or the ventricle septum of a heart or in a body channel.

PRIOR ART

WO 03/032818 describes an umbrella-style occluder, i.e. it is automatically deployed as soon as it leaves its deployment catheter. It comprises an occluding member with a frame and a barrier. The frame consists of a plurality of radially outwardly extending spokes. The barrier comprises two layers, with one layer on each side of the frame.

WO 2005/034723 shows an occluder with two sail-like occluding bodies, each arranged on a hoop. Arms are connecting the two hoops with a center post. The arms have a shape memory so that the occluder is deployed automatically in its desired shape.

EP 0 474 887 also describes a self-expanding sail-like occluder with two patches, each composed of a fabric sheet extended over a resilient annular frame. The two patches are arranged face-to-face with a gap in between and concentrically stitched to each other at a position inward the outer periphery of each patch. By drawing a thread appearing on one of the patches, both patches are brought closer to each other.

EP 1 149 561 discloses a spring-like septal defect occluder with two occluding panels. Each occluding panel includes a fabric support structure and fabric suspended therefrom.

WO 01/49185 shows a spring-like occluder with strings connecting elongate spring members.

WO 97/16119 refers to a self-centering umbrella-type septal closure device which includes a proximal and a distal occluder each having a plurality of arms supporting occlusion bodies. Each of the proximal and distal support arms has at least three coils.

U.S. Pat. No. 4,836,204 shows a double-balloon septal defect occlusion catheter which is used to temporarily close septal perforations, permitting elective surgical closures of the defect at a later date.

U.S. Pat. No. 3,874,388 discloses an occluder with two umbrellas, each umbrella is opened individually wherein the umbrellas are brought together and locked to each other within a human body passage.

WO 2010/151509 describes an occluder an expandable frame consisting of wires extending from a proximal end to a distal end of the frame. The wires form a proximal eyelet, an intermediate eyelet and a distal eyelet. The occluder further comprises a sealing member partially encapsulation the expandable wire frame. This sealing member is formed by sheets of a thin material adhered to the frame by an adhesive.

US 2008/0077180 shows an occluder with a tissue scaffold which encapsulates the occluder petals. This tissue scaffold is considered to improve the sealing of the aperture being closed.

A well-working implant for occluding a passage in a circulatory system is disclosed in U.S. Pat. No. 6,488,706. This implant has its particular application as a cardiological implant by means of which it is possible, for example to close an aperture through the atrial septum or the ventricle septum of a heart. It is arranged to be deployed or built up at a desired location in the body, unlike to known other implants which are instead extended as soon as a compressed umbrella or a compressed sail leaves its insertion catheter. This occluder comprises a plurality of thin wire-like elongate members which form a fixation structure and a single occluding body, namely a disk-like flexible membrane, which is expanded by the fixation structure in the body passage. The fixation structure is locked in its expanded state by a locking unit. This locking unit comprises two locking elements which are brought together when the occluding body is expanded.

WO 2005/074813 discloses an occluder working with the same principle but comprising two occluding bodies which are expanded by the fixation structure. This occluder securely closes both sides of the passage.

The two last mentioned occluders have the advantage that the occluders can be opened and closed and therefore its location within the body passage can be changed until the fixation structure is locked in its expanded form by the locking unit. However, care has to be taken that the thin elongate members, especially when bent into the fixation structure, do not break. When biodegradable material is used as suggested in US 2003/0149463, care has to be taken that the implant is overgrown with the body tissue, before the material is dissolved. Small parts which would otherwise break from the occluder and be transported in other parts of the human body, may cause some severe damage. Furthermore it was noticed that the overgrowth of the occluding body, especially the disk-like membranes, happens faster than the overgrowth of the elongate members.

SUMMARY OF THE INVENTION

It is therefore an object of the invention to provide an improved occluder.

The inventive occluder for occluding a passage in a circulatory system comprises at least one occluding body for occluding the passage,
an expanding unit comprising at least one fixation structure for fixing the occluding body within the passage, wherein at least a part of the expanding unit is expanding into said fixation structure thereby expanding the occluding body and a locking unit for locking the expanding unit in its expanded state,
wherein the expanding unit comprises a first and a second end and wherein the first end is attached to a first element of the locking unit and the second end is attached to a second element of the locking unit, the first and second elements of the locking unit being brought in locking engagement with each other when the occluding body is expanded,
wherein the occluder further comprises a jacket which envelops at least a part of the expanding unit.

In case the expanding unit is a multiple of elongate members, such as filaments, threads or wires, the outer jacket can envelop a multiple or all of these elongate members, i.e. a bunch of them. There can also be a multiple of jackets and each elongate member or at least some of these elongate members are enveloped with a separate jacket each. In another embodiment, the elongate members are enveloped individually on a part of their length or over their whole length and they are in addition enveloped as a bunch with additional jackets. For example, the fixation structures are enveloped as a whole and the remaining parts of the elongate members between the two membranes or occluding bodies are enveloped individually.

The occluder according to the invention comprises a protecting jacket or shell at least for the fixation structure. This shell is made of a soft and/or flexible material so that it can also be compressed or folded when the occluder is introduced in an introduction sheath into the animal or human body. This jacket surrounds and envelops the fixation structure. Preferably it is always arranged around this part of the expanding unit, even before the fixation structure is formed; i.e. before the occluder is expanded.

When parts of the fixation structure break away, they are hold back by the jacket and can not wander through the body. It is a further advantage, that in case the cavity with the jacket gets filled with coagulated blood the fixation structure is embedded and broken parts do not wander.

In a preferred embodiment, the jacket surrounds the fixation structure in its circumference around the longitudinal axis of the occluder. In another preferred embodiment, the jacket surrounds single parts of the expanding unit. If the expanding unit consists of elongate members such as filaments, each or at least some of the elongate members can be encapsulated in a jacket along its whole length or along a part of its length.

The jacket in all embodiments can be made of a tight material or it can also have openings. For example it can be a net, knitted fabric, woven fabric or a casted membrane.

It is a further advantage that the jacket, sheath or envelope enhances the endotheliasation or overgrowth of occluder and tissue since tissue cells prefer the material of the jacket more than the material of the fixation structure. This enhances the overgrowth of the occluder especially in embodiments where the fixation structure adapts its shape to the tissue surrounding of the passage in the human or animal body.

Preferred material for the jacket is Polyester or a degradable polymer like PLA, PLLA, PGA, PLGA or P4HB or a blend of those polymer materials. Preferred material for the fixation structure is metal or a degradable polymer like PLA, PLLA, PGA, PLGA or P4HB or a blend of those polymer materials. The occluding body is preferably made of the same material as the jacket. However it can be made of a different material as well. Preferred materials for the occluding body are Polyester or a degradable polymer like PLA, PLLA, PGA, PLGA or P4HB or a blend of those polymer materials. The occluding body is preferably made of a flexible sheet. Preferably it has a circular disk-like shape when expanded.

When an occluder is used which has two jackets, the jackets can be made of different materials. For example one of them can be biodegradable and the other one is not. The same applies for the fixation structures and for the occluding bodies.

When the jacket is made of a biodegradable material, the fixation structure is preferably made of a biodegradable material as well. In a preferred embodiment, the rate of degradation of the jacket is smaller than the one of the fixation structure so that the fixation structure is protected by the jacket until it is well dissolved or the occluder is overgrown.

In a preferred embodiment of the invention the occluder comprises exactly two fixation structures and two outer jackets, each jacket enveloping one of the fixation structures. This embodiment can comprise one single occluding body or two occluding bodies.

In a preferred embodiment, the occluder comprises exactly a first and a second occluding body, wherein the first and second occluding bodies are arranged at a distance from each other, wherein a first of said fixation structures is arranged between the first occluding body and the first element of the locking unit and a second of said fixation structures is arranged between the second occluding body and the second element of the locking unit. This arrangement enables a secure closure of both sides of the passage.

The expanding unit can be made in different shapes and embodiments. Preferably comprises the expanding unit a plurality of elongate members such as filaments or wires with first and second ends each, wherein the first end of each elongate member is attached to a first element of the locking unit and the second end of each elongate member is attached to a second element of the locking unit and wherein these elongate members are twisted to form the at least one fixation structure. Preferably the occluder is made according to the ones described in U.S. Pat. No. 6,488,706, WO 2005/074813 and US 2003/0149463.

Preferably, the expanding unit is movable relative to the enveloping jacket. Like this the fixation structure can be built up within its shell without being disturbed while expanding Preferably, the jacket is attached to at least some of the elongate members, wherein the elongate members comprise a longitudinal axis each and wherein the elongate members can move relative to the jacket in direction of their corresponding longitudinal axis. Like this the fixation structure is not disturbed while expanding but it is ensured that the jacket will safely surround the fixation structure when built up. Sewing the jacket on at least some of the longitudinal members is one simple way to obtain a secure but still loose connection between fixation structure and jacket.

In a preferred embodiment, the fixation structure is expanded within the jacket, but does not penetrate the material of the jacket.

Preferably the jacket is attached to the occluding body. The occluding body can form one side of the jacket. In a preferred embodiment, the occluding body has a circumferential rim and the jacket is fixed to this rim. This attachment does not have to be leak-proof but can have holes or openings. For example, the jacket can be sewed onto the occluding body, it can be welded onto it, it can be glued to it or otherwise connected. It is also possible that occluding body and jacket are made of one single unitary part. However in all embodiments it is preferred that the occluding body has a round and approximately flat disk-like shape when the occluder is expanded. Jacket and occluding body are preferably made of a flexible material, wherein the occluding body and the jacket are compressible into a folded state.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

The occluder according to the preferred embodiments is based on the implants disclosed in WO 2005/074813. However, it can also be based on an occluder as described in U.S. Pat. No. 6,488,706 and US 2003/0149463, i.e. an occluder with a single occluding body. The occluder according to the invention could also have another shape and can function in another way as described below.

The occluder according to FIGS. 1 to 9 is used as an implant for closing an internal passage, for example an aperture in the atrial septum or the ventricle septum of a heart, a left atrial appendage or in another human or animal body channel which one wishes to close, the implant is compressible for insertion through a delivery mechanism, such as an introduction sheath introduced in a body vein or artery or body vessel, and is deployable or expansible for occluding the passage in the circulatory system when arrived at the position of the intended closing spot.

Figure 1:
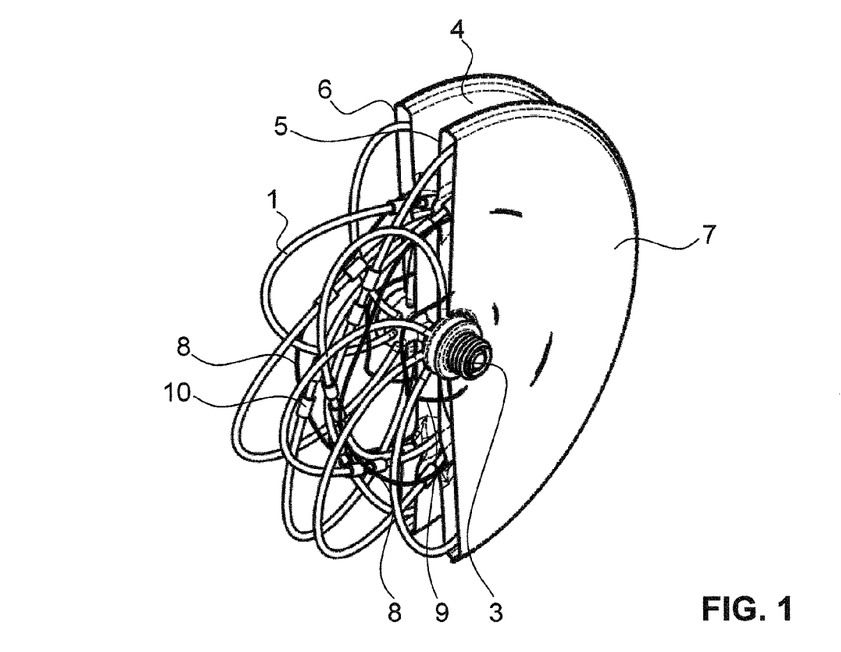
FIG. 1 shows a partial sectional view of an occluder according to the invention in an expanded state in a first embodiment.
Figure 2:
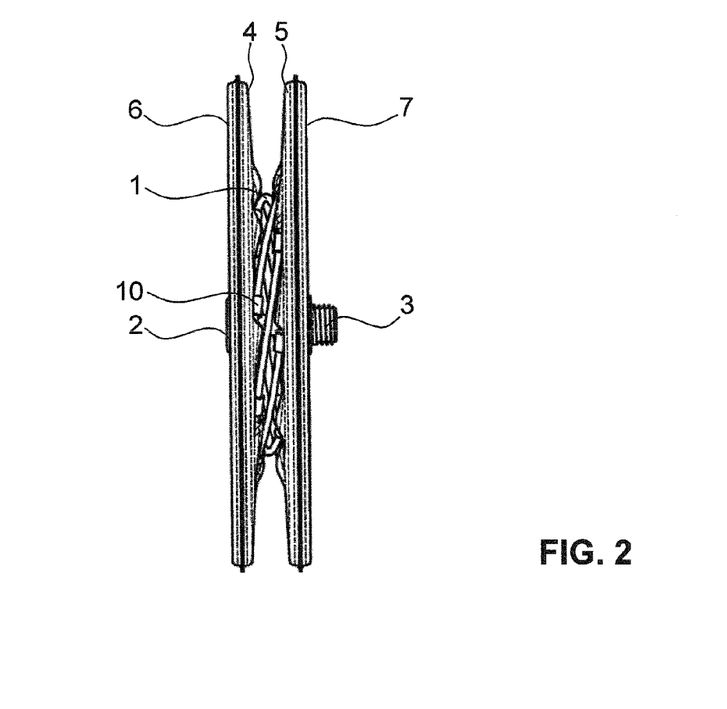
FIG. 2 shows a side view of the occluder according to FIG. 1.
Figure 3:
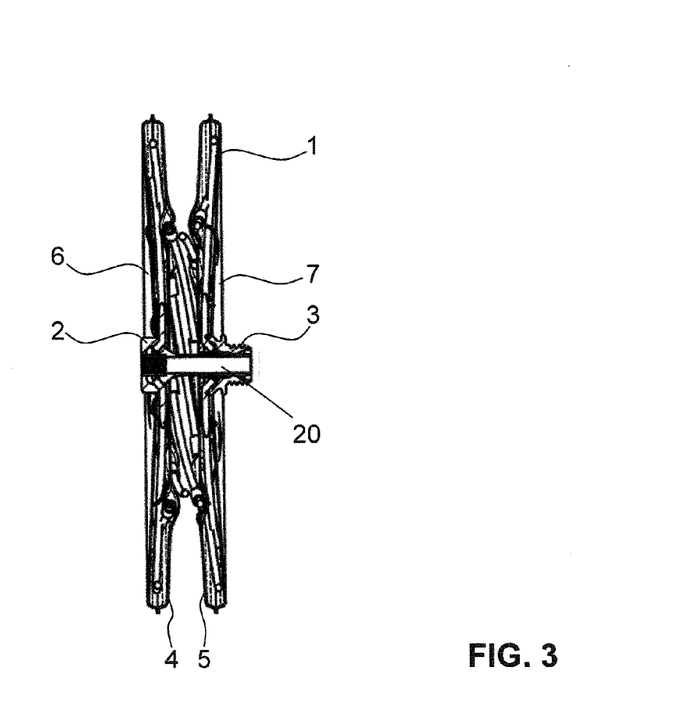
FIG. 3 shows a longitudinal section of the occluder according to FIG. 1.
Figure 4:
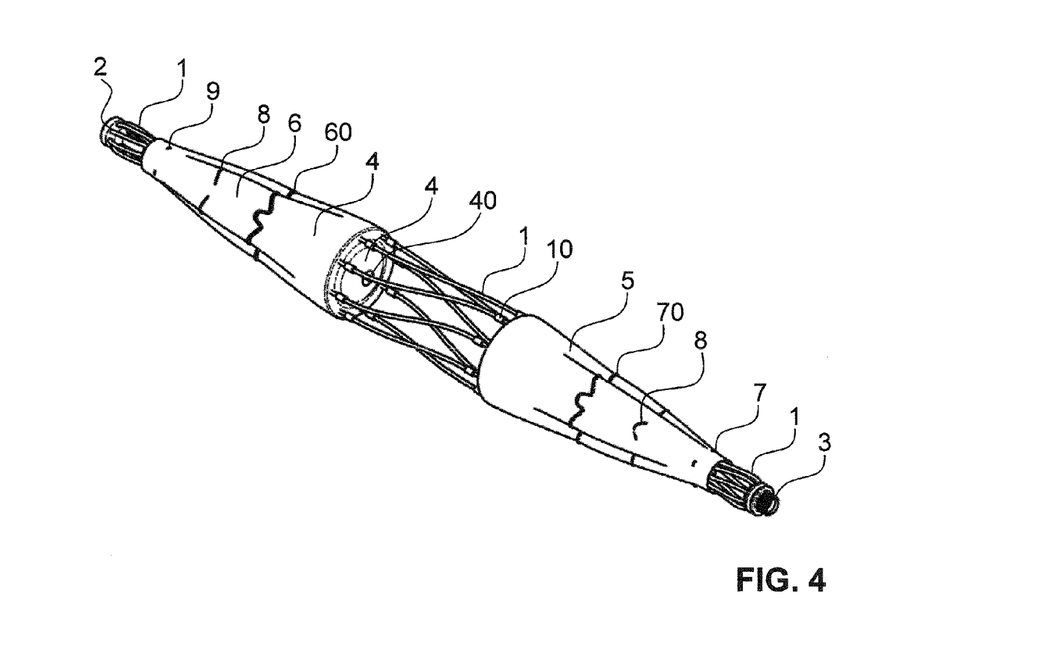
FIG. 4 shows the occluder according to FIG. 1 in an almost completely compressed state.
Figure 5:
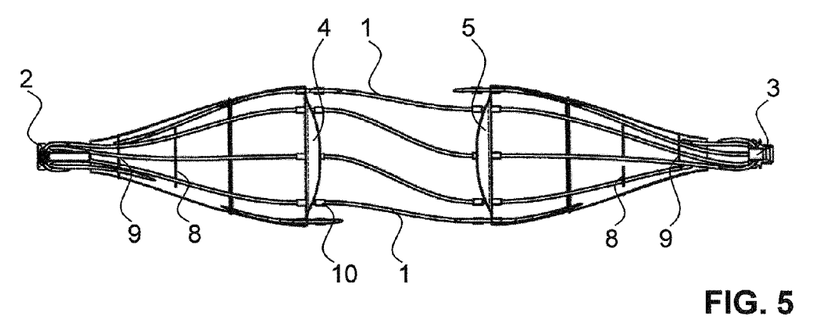
FIG. 5 shows the occluder according to FIG. 1 in a partly deployed or expanded state in a longitudinal section.
Figure 6:
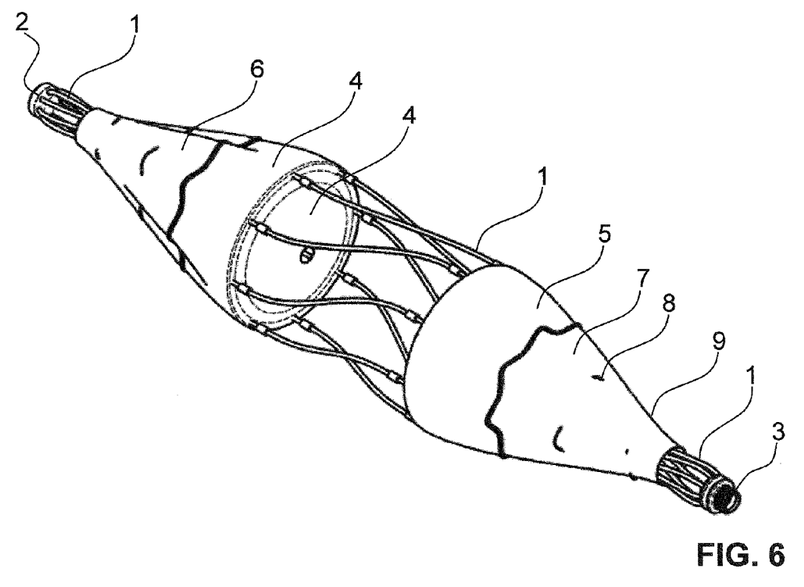
FIG. 6 shows the occluder according to FIG. 5 in a perspective view.
Figure 7:
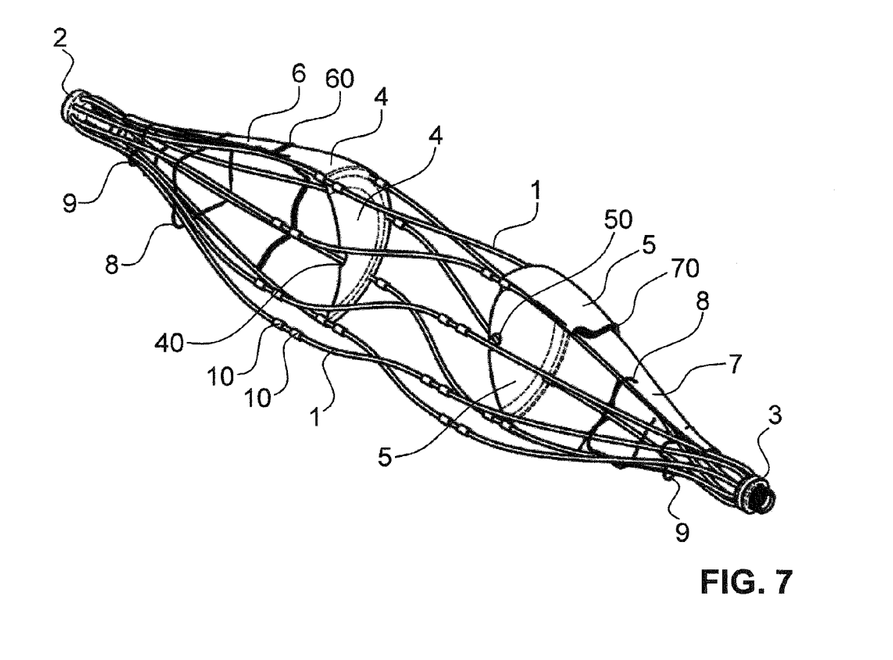
FIG. 7 shows the occluder according to FIG. 5 in a partial longitudinal section.
Figure 8:
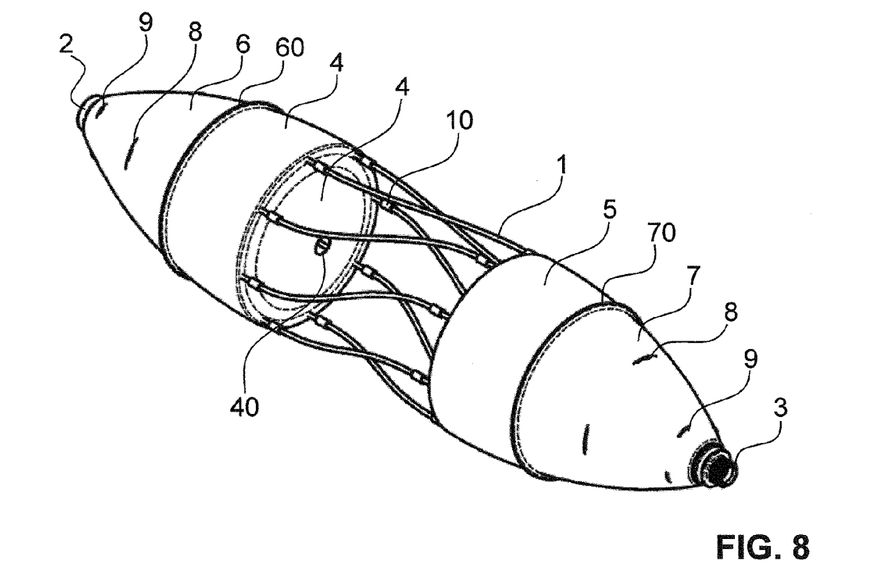
FIG. 8 shows the occluder according to FIG. 1 in a more deployed state compared to FIG. 5.

The occluder comprises at least one, here two occluding bodies 4, 5, an expanding unit 1 and a locking unit 2, 3, as can be seen in FIGS. 1 to 3.

The expanding unit consists of a plurality of thin elongate members 1. These elongate members 1 are like filaments, wires or threads. They are flexible and can be bent, but preferably they have no elasticity in direction of their longitudinal axis. They are preferably stiff and inextensible. Each elongate member has a first end which is attached to or hold in a first holder 2 and a second end, which is attached to or hold in a second holder 3. The elongate members 1 are arranged separate from each other and are not directly connected to each other; i.e. they are preferably separate wires and not part of a net or otherwise connected.

When the two holders 2, 3 are brought together, the elongate members 1 are compressed longitudinally. They automatically bend and twist sideways to form two circular or loop shapes, similar to a flower, a propeller or an umbrella. These twisted shapes form fixation structures. These structures lay, when the occluder is implanted, on the surrounding tissue on both sides of the passage to be closed and fix the occluder at this position.

Figure 9:
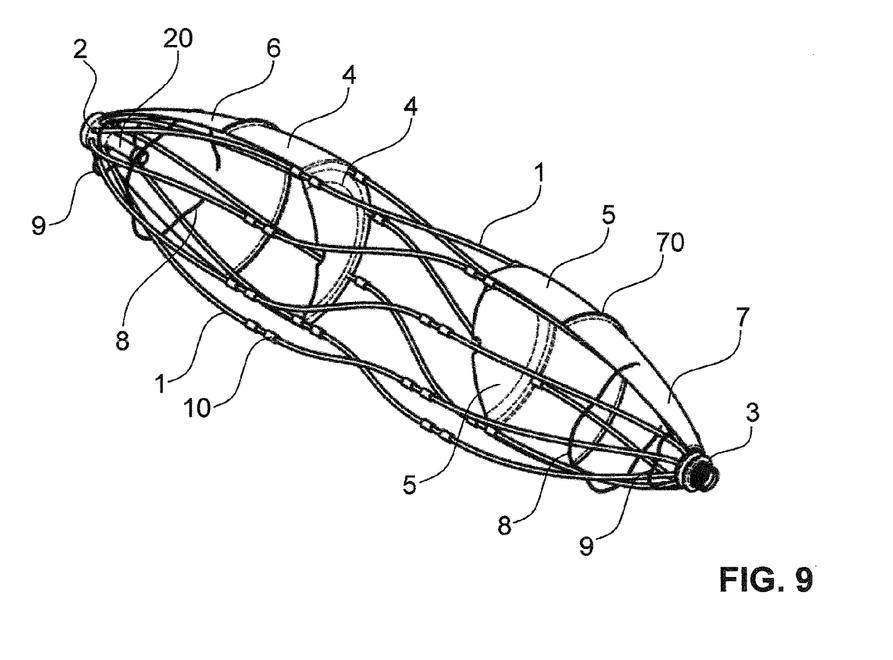
FIG. 9 shows the occluder according to FIG. 8 in a partial longitudinal section.

The two holders 2, 3 have locking elements which lock the occluder in this expanded shape and therefore lock the fixation structures in their shapes. One locking element is best seen in FIG. 9. It is a locking stem 20 of the first holder 2, which can be brought in engagement with an opening in the second holder 3. This situation is best seen in FIG. 3.

Figure 12:
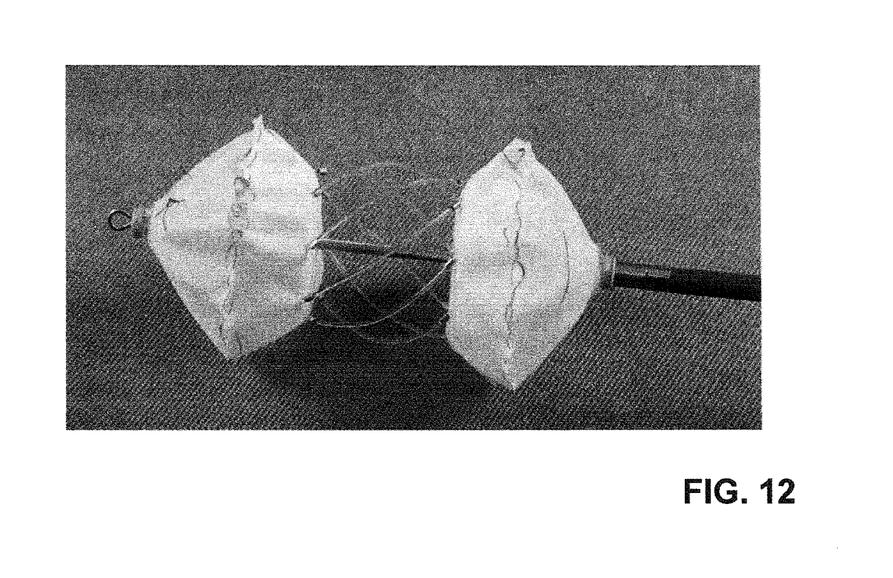
FIG. 12 shows a photo of the inventive occluder according the first embodiment.

The first and second occluding bodies 4, 5 are thin membranes, which are located between the two holders 2, 3. In their extended shape, they are preferably round, disk-shape and almost flat. They are made of a flexible material so that they can be folded or compressed when introduced into the introduction sheath. In the extended and deployed state of the occluder, they are extended as well. Preferably, they are almost flat, but they are usually not stretched in this position so that they can abut the surrounding tissue of the passage to be closed. In the figures, the occluding bodies appear to be quite stiff and their compressed and actual flexible shape are not realistically shown. Especially FIGS. 1 and 2 should not be understood in a way that the membranes 4, 5 and the jackets 6, 7 (which will be described later on) are stretched. Furthermore, in the situations shown in FIGS. 4 to 9 the two membranes 4, 5 are realistically more folded and less flat disk-like. The photo according to FIG. 12 shows the real occluder. The seems 60 and 70, dividing the membranes 4, 5 from the jackets 6, 7 can well be seen. Preferably, the two occluding bodies 4, 5 are made of the same material each and have preferably the same size and shape each.

The occluding bodies 4, 5 extend in a radially manner from the longitudinal axis of the elongate members 1. Preferably they are arranged concentrically to this axis. Also preferably, both membranes are identical and their distance to their neighboring holder 2, 3 is identical. Each occluding body 4, 5 comprise a central hole 40, 50. These holes 40, 50 as well as corresponding holes in the two holders 2, 3 are penetrated by a guide wire when the occluder is introduced with an introduction sheath into the body passage.

The occluding bodies 4, 5 comprise on their circumference, in a substantial distance to their circumferential edge, holes which are penetrated by the elongate members 1. This can best be seen in FIGS. 5 and 6. The holes are preferably arranged in evenly distances from each other. The elongate members 1 preferably comprise fixation bushes 10 on both sides of the membranes 4, 5, which enable the membranes 4, 5 to move for only a short distance along the elongate members 1. Theses bushes 10 can also be used as X-ray markers, especially when the elongate members are invisible for X-ray. The bushes 10 are preferably made of metal, such as platinum-iridium or of a degradable but X-ray-visible material such as a blend of a polymer with BaS.

The occluding bodies 4, 5 divide each of the elongate members 1 in three portions. A first portion lies between the first holder 2 and the first membrane 4. A second portion lies between the two membranes 4, 5 and the third portion lies between the second membrane 5 and the second holder 3. The first and third portions form in the expanded and twisted position the first and second fixation structure. The second portion has in this state a coil-like shape, as can best be seen in FIG. 2. Preferably at least the first and third portions of the elongate members 1 have the same length.

According to the invention, each flower-like fixation structure is individually surrounded by an own protecting jacket 6, 7 or shell. A first jacket 6, which is preferably a sleeve, is arranged around the first portion of the elongate members 1 and a second, preferably identical jacket 7 is arranged around the third portion of the elongate members 1. This can best be seen in FIGS. 4, 6, 8 and 9.

The elongate members 1 can move relative to the jackets 6, 7. However to fix the position of the jackets 6, 7 so that they always lay over the first and third portions, the jackets 6, 7 are loosely attached to at least some of the elongate members 1 in this region. This is done in this example by threads 8, 9, so that the jackets 6, 7 are sewed to the elongate members 1. This can best be seen in FIGS. 5, 7 and 9.

The jackets 6, 7 themselves can be made of one single piece or they can be made of several parts which are connected to each other. In this example they are made of one single part each and are sewed to the membranes 4, 5 with sewing seams 60, 70.

The jackets 6, 7 are also attached to the membranes 4, 5, wherein the membranes 4, 5 form one face side of the jackets 6, 7. Preferably the jackets 6, 7 are sewed to the membranes 4, 5, so that they form a closed envelope or flexible shell which is open only for to small central holes on each side which are penetrated by the elongate members 1. Each occluding bodies 4, 5 however does always preferably form an approximately flat element when deployed and expanded, so that the occluding bodies 4, 5 can smoothly abut the surrounding tissue of the passage and close the passage in the most appropriate way.

As can best be seen in FIGS. 1 and 3 the fixation structures are enclosed within the shell formed by the jackets 6, 7 and the membranes 4, 5. Nevertheless, the fixation structure can still adapt its shape to the anatomical surrounding of the passage to be closed. As can be seen in FIGS. 4 to 9 the parts of the expanding unit, i.e. the elongate members 1, which form the fixation structure in the expanded state, are also enclosed in these shells in the compressed or partly deployed state.

Figure 10:
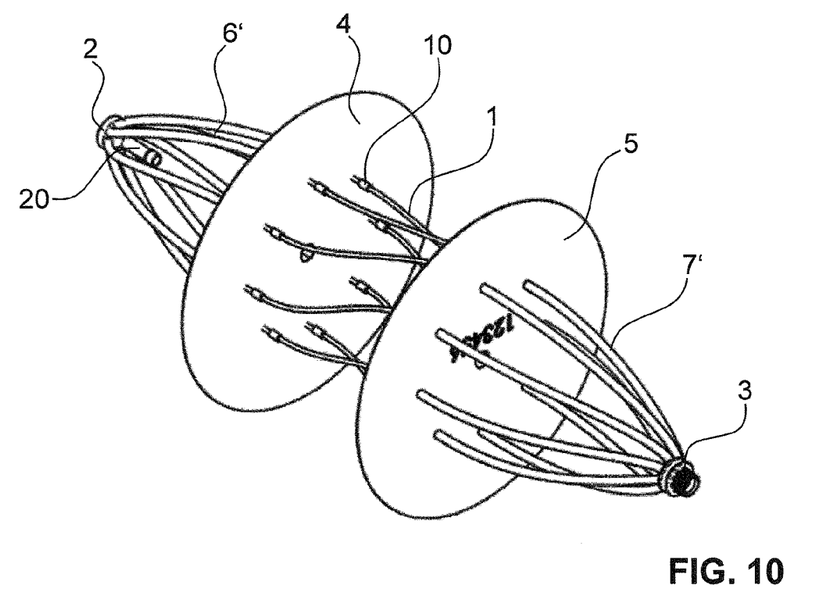
FIG. 10 shows an inventive occluder according to a second embodiment.

FIG. 10 shows the inventive occluder according to a second embodiment. The elongate members 1 are enveloped in jackets 6' and 7' each. The jackets 6' are arranged between first holder 2 and first membrane 4. The second jackets 7' are arranged between second holder 3 and second membrane 5. Between the two membranes 4, 5, the elongate members 1 are free and not encapsulated. Preferably the elongate members 1 can still move free relative to the jackets 6', 7'.

Figure 11:
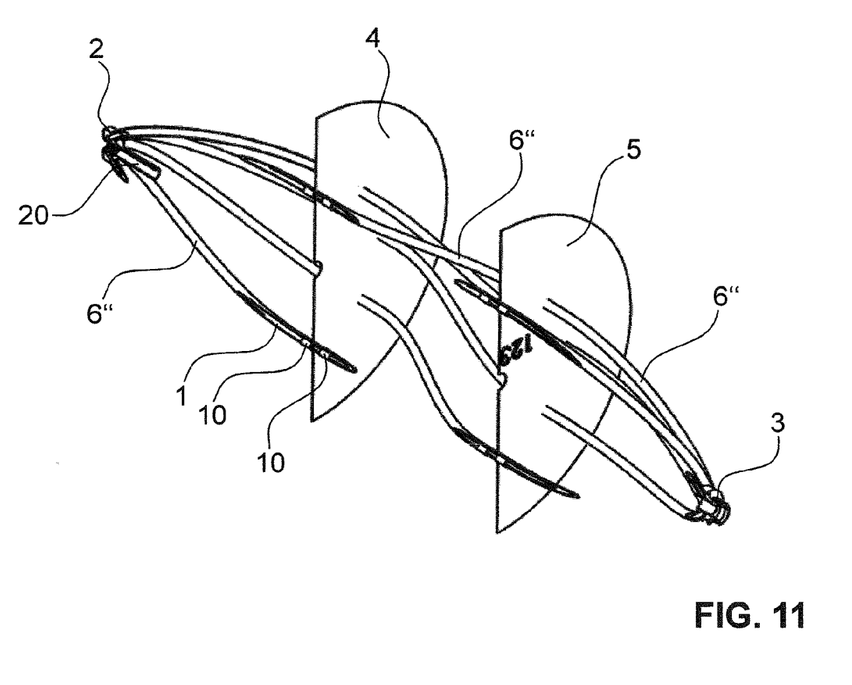
FIG. 11 shows an inventive occluder according to a third embodiment.

FIG. 11 shows a third embodiment of the inventive occluder. Here a long jacket 6'' which extends from the first to the second holder 2, 3 encapsulates at least approximately the whole length of each elongate member 1. The bushes 10 are also encapsulated within this jacket 6''. Once again the elongate member 1 can preferably still move relative to his jacket 6'' in its longitudinal direction. The long jacket 6'' can also be made of more than one part, for example three parts, so that the jacket is divided into three pieces by the two membranes 4, 5.

Figure 13:
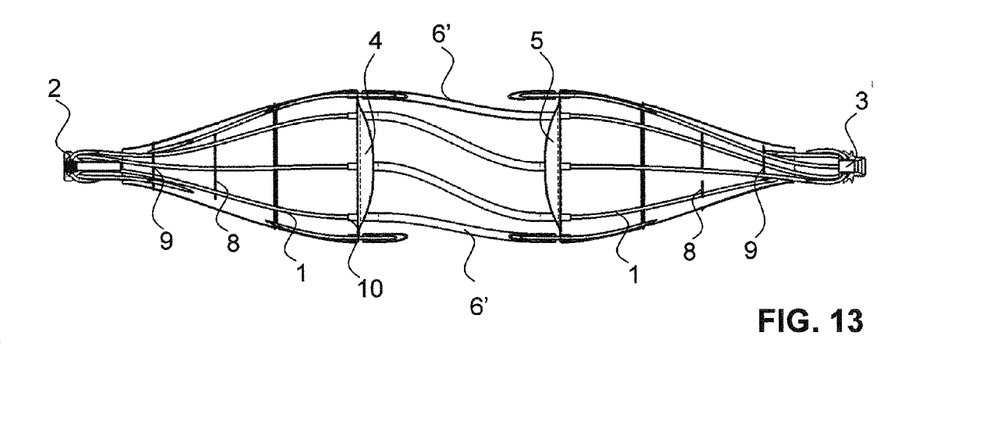
FIG. 13 shows an inventive occluder according to a fourth embodiment, in partly deployed or expanded state in a longitudinal section.
Figure 14:
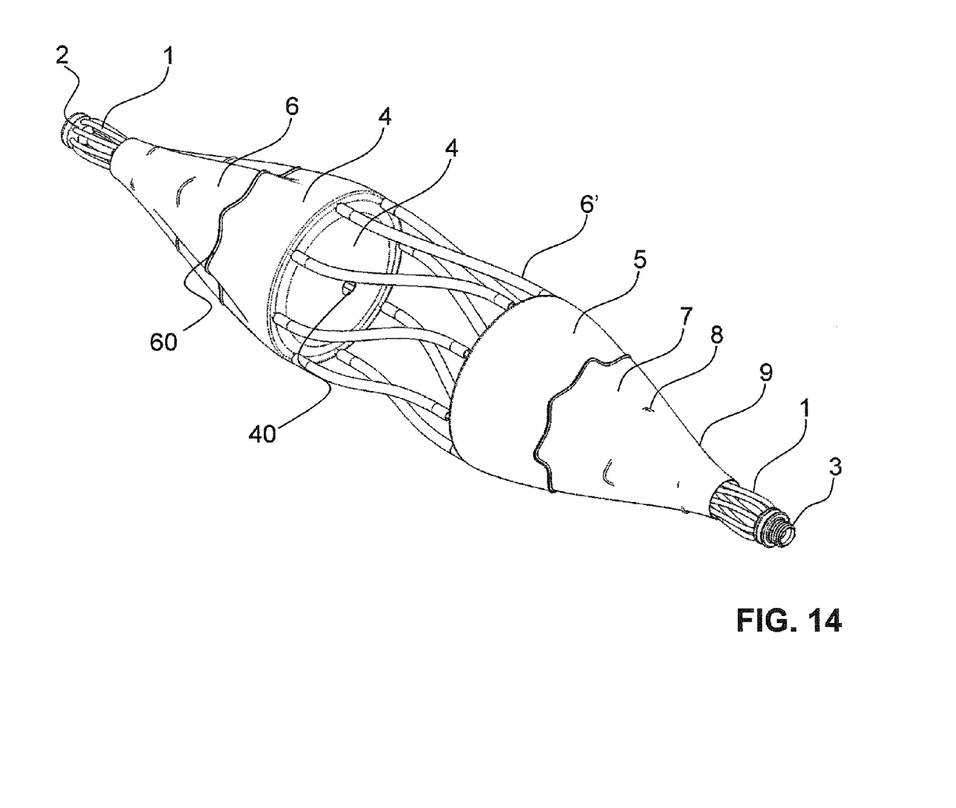
FIG. 14 shows the occluder according to FIG. 13 in a perspective view.
Figure 15:
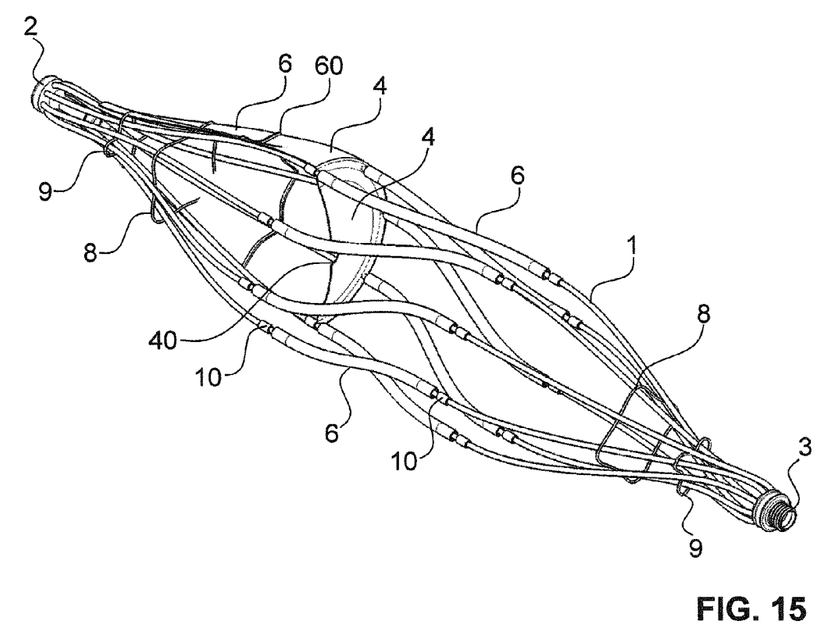
FIG. 15 shows the occluder according to FIG. 13 missing one sheath and one occluding body.

FIGS. 13 to 15 show a fourth embodiment of the inventive occluder. This embodiment comprises the first and second jackets 6, 7, enveloping the two fixations structures on the distal and the proximal side of the occluder. These jackets 6, 7 are sleeves, arranged around the first and third portion of the bunch of elongate members 1. The jackets 6, 7, are preferably sewed to the elongate members 1 and to the membranes 4, 5. In addition this embodiment comprises a multiple of third jackets 6', arranged between the first and the second membrane 4, 5, wherein these third jackets 6' surround a single elongate member 1 each. As can best be seen in FIG. 15, they preferably only envelop the elongate members 1 partially, i.e. only between the two membranes 4, 5. Preferably, they are held in place by the threads 10 or the membranes 4, 5 themselves. The remaining parts of the elongate members 1 are enveloped as a bunch by the first and second jackets 6, 7.

The occluder according to the invention ensures that no parts of the occluder can wander within the human or animal body and enhances the growth of the body tissue over the occluder.

The invention claimed is:

1. Occluder for occluding a passage in a circulatory system, the occluder comprising at least one occluding body for occluding the passage,
   an expanding unit comprising at least one fixation structure for fixing the occluding body within the passage, wherein at least a part of the expanding unit is expanding so as to form said fixation structure thereby expanding the occluding body, and
   a locking unit for locking the expanding unit in its expanded state, the locking unit having a first element and a second element,
   wherein the occluder comprises a protecting jacket which envelops at least a part of said expanding unit,
   wherein the first and second elements of the locking unit can be brought in locking engagement with each other when the occluding body is expanded,
   wherein the expanding unit comprises a plurality of elongate members with first and second ends each, wherein the first end of each elongate member is attached to the first element of the locking unit and the second end of each elongate member is attached to the second element of the locking unit, wherein the elongate members can be twisted to form the at least one fixation structure,
   wherein the at least one occluding body is a flexible sheet,
   wherein the at least one occluding body comprises on its circumference holes which are penetrated by the elongate members, and
   wherein the expanding unit is movable relative to the protecting jacket.

2. Occluder according to claim 1 wherein the protecting jacket is attached to the at least one occluding body.

3. Occluder according to claim 1 wherein the protecting jacket envelops at least one of said fixation structure.

4. Occluder according to claim 1 wherein the occluder comprises exactly two fixation structures and two outer protecting jackets, each protecting jacket enveloping one of the fixation structures.

5. Occluder according to claim 1 wherein the occluder comprises exactly a first and a second occluding body, wherein in a non-expanded state the first and second occluding bodies are arranged at a distance from each other, wherein a first of said fixation structures is arranged between the first occluding body and the first element of the locking unit and a second of said fixation structures is arranged between the second occluding body and the second element of the locking unit.

6. Occluder according to claim 5 wherein the protecting jacket is sewed on at least some of the elongate members.

7. Occluder according to claim 1 wherein the protecting jacket is surrounding the plurality of elongate members and wherein the protecting jacket is attached to at least some of the elongate members, wherein the elongate members comprise a longitudinal axis each and wherein the elongate members can move relative to the protecting jacket in direction of their corresponding longitudinal axis.

8. Occluder according to claim 1 wherein the fixation structure is expanded within the protecting jacket.

9. Occluder according to claim 1 wherein the occluding body has a circumferential rim and wherein the protecting jacket is fixed to the occluding body at a distance to this rim.

10. Occluder according to claim 1 wherein the protecting jacket is made of a flexible material and wherein the protecting jacket is compressible into a folded state.

11. Occluder according to claim 1 wherein a multiple of protecting jackets are present which envelop at least a part of the expanding unit and wherein each elongate member is enveloped in a separate of said protecting jackets.

12. Occluder according to claim 1 wherein the occluder comprises exactly two fixation structures and two occluding bodies expanded by said fixation structures and wherein the elongate members are enveloped individually at least along their length extending between the two occluding bodies.

\* \* \* \* \*